(12) United States Patent
Elliott

(10) Patent No.: US 9,999,766 B2
(45) Date of Patent: Jun. 19, 2018

(54) DEVICE FOR VERIFYING THE ELECTRICAL OUTPUT OF A MICROCURRENT THERAPY DEVICE

(75) Inventor: Charles Richard Elliott, Leeds (GB)

(73) Assignee: Synapse Electroceutical Limited, Westerham, Kent (GB)

( * ) Notice: Subject to any disclaimer, the term of this patent is extended or adjusted under 35 U.S.C. 154(b) by 605 days.

(21) Appl. No.: 13/130,096

(22) PCT Filed: Nov. 20, 2009

(86) PCT No.: PCT/GB2009/002728
§ 371 (c)(1),
(2), (4) Date: Aug. 4, 2011

(87) PCT Pub. No.: WO2010/058184
PCT Pub. Date: May 27, 2010

(65) Prior Publication Data
US 2011/0279280 A1    Nov. 17, 2011

(30) Foreign Application Priority Data
Nov. 20, 2008 (GB) .................................. 0821280.5

(51) Int. Cl.
*A61N 1/08* (2006.01)
*A61N 1/32* (2006.01)

(52) U.S. Cl.
CPC ................. *A61N 1/32* (2013.01); *A61N 1/08* (2013.01); *A61N 1/326* (2013.01)

(58) Field of Classification Search
CPC ................. A61N 1/0472; A61N 1/326; A61N 1/326021; A61N 1/0456
USPC ........................................................ 607/115
See application file for complete search history.

(56) References Cited

U.S. PATENT DOCUMENTS

| 3,886,931 | A | * | 6/1975 | Rodler | A61N 1/32 |
| | | | | | 600/554 |
| 4,088,141 | A | | 5/1978 | Niemi | |
| 4,613,850 | A | | 9/1986 | Timmermann | |
| 4,982,742 | A | * | 1/1991 | Claude | 607/50 |
| 5,395,398 | A | * | 3/1995 | Rogozinski | 607/50 |

(Continued)

FOREIGN PATENT DOCUMENTS

| GB | 2374533 | 10/2002 |
| GB | 2406519 | 4/2005 |

(Continued)

OTHER PUBLICATIONS

International Search Report for PCT/GB2009/002728 dated Jan. 26, 2010.
UK Search Report for GB0821280.5 dated Mar. 19, 2009.

*Primary Examiner* — Amanda Patton
(74) *Attorney, Agent, or Firm* — Christopher M. Scherer; DeWitt Ross & Stevens S.C.

(57) ABSTRACT

A device and method verifies the electrical output of a microcurrent therapy device. The current and/or voltage of an electrical pulse, being supplied to an electrode adapted to contact tissue, is measured by a control unit. The current and/or voltage is supplied by the control unit according to a predefined waveform. Any difference in the current or voltage of the electrical pulse being supplied with respect to the current or voltage of the predefined waveform is detected.

18 Claims, 3 Drawing Sheets

(56) References Cited

U.S. PATENT DOCUMENTS

| | | | |
|---|---|---|---|
| 5,458,623 A * | 10/1995 | Lu | A61N 1/371 607/28 |
| 5,725,563 A | 3/1998 | Klotz | |
| 5,935,156 A * | 8/1999 | Chandler et al. | 607/66 |
| 6,249,706 B1 * | 6/2001 | Sobota et al. | 607/115 |
| 6,411,853 B1 * | 6/2002 | Millot et al. | 607/50 |
| 6,445,955 B1 * | 9/2002 | Michelson et al. | 607/46 |
| 6,505,079 B1 * | 1/2003 | Foster | A61N 1/08 607/63 |
| 7,158,834 B2 * | 1/2007 | Paul, Jr. | 607/48 |
| 8,644,942 B1 * | 2/2014 | Diemer | 607/51 |
| 2003/0074037 A1 * | 4/2003 | Moore et al. | 607/63 |
| 2003/0097153 A1 * | 5/2003 | Bardy | A61N 1/3956 607/5 |
| 2004/0010290 A1 * | 1/2004 | Schroeppel et al. | 607/3 |
| 2004/0173220 A1 * | 9/2004 | Harry et al. | 128/892 |
| 2004/0254613 A1 * | 12/2004 | Ostroff | A61N 1/3956 607/5 |
| 2005/0033381 A1 * | 2/2005 | Carter | A61N 1/326 607/46 |
| 2005/0222623 A1 * | 10/2005 | Kroll et al. | 607/2 |
| 2005/0278001 A1 * | 12/2005 | Qin et al. | 607/48 |
| 2006/0052844 A1 | 3/2006 | Newman | 607/67 |
| 2006/0142817 A1 * | 6/2006 | Chandler | 607/50 |
| 2006/0167503 A1 * | 7/2006 | Warren | A61N 1/3943 607/5 |
| 2006/0167504 A1 * | 7/2006 | Warren | A61N 1/3943 607/5 |
| 2006/0184211 A1 * | 8/2006 | Gaunt et al. | 607/48 |
| 2006/0259089 A1 * | 11/2006 | Kim | A61B 5/0464 607/14 |
| 2007/0038275 A1 * | 2/2007 | Kim | 607/90 |
| 2008/0103549 A1 * | 5/2008 | Wenzel et al. | 607/50 |
| 2009/0030477 A1 * | 1/2009 | Jarrard | A61B 18/1206 607/42 |
| 2010/0131024 A1 * | 5/2010 | Lathrop et al. | 607/3 |

FOREIGN PATENT DOCUMENTS

| | | |
|---|---|---|
| GB | 2432320 | 5/2007 |
| GB | 2432321 | 5/2007 |
| GB | 2432322 | 5/2007 |
| GB | 2432323 | 5/2007 |
| WO | 9920341 | 4/1999 |

* cited by examiner

DEVICE FOR VERIFYING THE ELECTRICAL OUTPUT OF A MICROCURRENT THERAPY DEVICE

CROSS-REFERENCE TO RELATED APPLICATIONS

This application is the U.S. national stage application of International Application PCT/GB2009/002728, filed Nov. 20, 2009, which international application was published on May 27, 2010, as International Publication WO2010/058184 in the English language. The International Application claims priority of Application No. GB0821280.5, filed Nov. 20, 2008.

FIELD OF THE INVENTION

The present invention relates to a method and device for verifying the electrical output of a microcurrent therapy device, in particular for verifying that the electrical output is being correctly supplied.

BACKGROUND OF THE INVENTION

Microcurrent therapy devices are well known in the prior art. Such devices are used in the treatment of animal or human tissue, for example damaged skin tissue which might have wounds or muscle tissue that might be torn. Typically, such devices comprise a control unit which is connected to electrodes. The control unit supplies a current, typically in the range of 0 to 1000 µA through electrodes which are in contact with the damaged tissue or overlaying tissue. There may be two electrodes, namely a positive and a negative electrode, and the control unit comprises a current generator which supplies current at a particular level from one electrode to the other electrode. The current that is being supplied has a particular predefined waveform, for example an analogue alternating current (AC) waveform or a square-tooth pulse waveform, having both positive and negative components at particular times in a cycle. The current generator attempts to regulate current at a level demanded by the predefined waveform, which may be user-selected. This is done by controlling the voltage across the electrodes. The voltage is varied because the resistance to current flow through tissue varies according to a number of factors, for example tissue thickness, distance between the electrodes, resistance to electrical current and contact between the electrodes and tissue.

The present applicant has previously applied for and been granted United Kingdom patent nos. 2406519, 2432323, 2432320, 2432321 and 2432322 relating to devices having control units which output various forms of waveforms. These waveforms have been determined to be significant in the repair of damaged tissue through the supply of microcurrent through the tissue. The disclosure in the aforementioned patents is incorporated herein by reference.

The control unit and electrodes are normally supplied and packaged as separate components; the control unit must be connected to electrodes prior to use. In this regard, the electrodes must be placed into good electrical contact with the tissue to ensure effective treatment. These tasks are often undertaken by the individual requiring treatment or another unskilled operator of the device, for example someone that is not a medical practitioner. This often means that the device may not end up being correctly connected to the electrodes or the electrodes may not end up being placed in good contact with the tissue to provide effective treatment.

SUMMARY OF THE INVENTION

The present invention, as defined in the appending claims, aims to solve the aforementioned problems. The present invention provides an indication via the control unit as to whether the device has been correctly connected to electrodes and placed into contact with tissue for effective treatment to take place.

In the first aspect of the present invention, there is provided a microcurrent therapy device, comprising:
 a control unit adapted to output an electrical signal to an electrode adapted to contact tissue, the current and/or voltage of the electrical signal being supplied according to a predefined waveform,
 wherein the control unit is further adapted to measure the current and/or voltage of the electrical signal being supplied and detect a difference in the current or voltage of the electrical pulse being supplied with respect to the current or voltage of the predefined waveform.

Thus, any variation in the voltage or current supplied to tissue can be detected and used to indicate an error in the device and/or electrode configuration.

In a second aspect of the present invention, there is provided a method for verifying the electrical output of a microcurrent therapy device, comprising:
 measuring the current and/or voltage of an electrical pulse being supplied to an electrode adapted to contact tissue, the current and/or voltage being supplied according to a predefined waveform;
 detecting a difference in the current or voltage of the electrical pulse being supplied with respect to the current or voltage of the predefined waveform.

In a third aspect of the present invention, there is provided a tissue dressing comprising the aforementioned microcurrent therapy device. Thus, any variation in the voltage or current supplied to tissue can be detected and used to indicate an error in the integrated device/tissue configuration.

BRIEF DESCRIPTION OF THE DRAWINGS

The present invention is described by way of reference to the accompanying drawings in which.

DETAILED DESCRIPTION OF THE INVENTION

Figure 1:
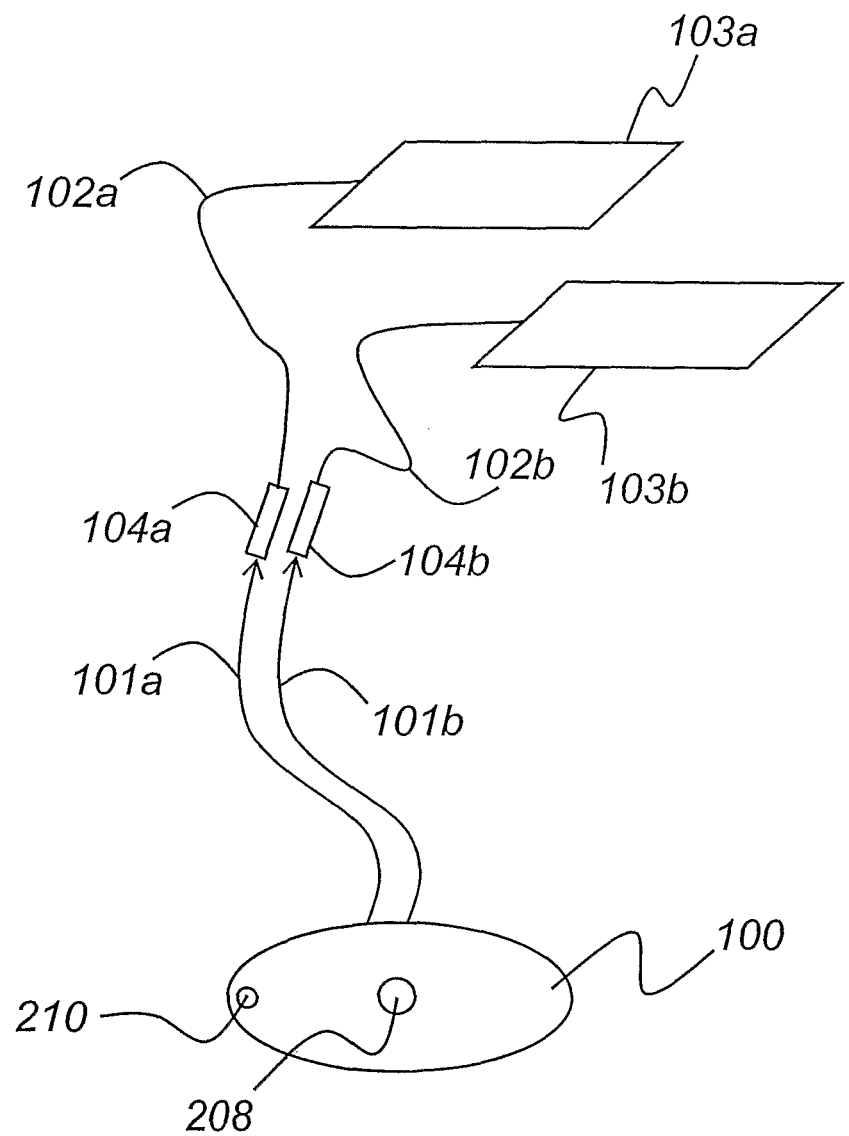
—
 FIG. 1 is a microcurrent therapy device according to one embodiment of the present invention.
Figure 2:
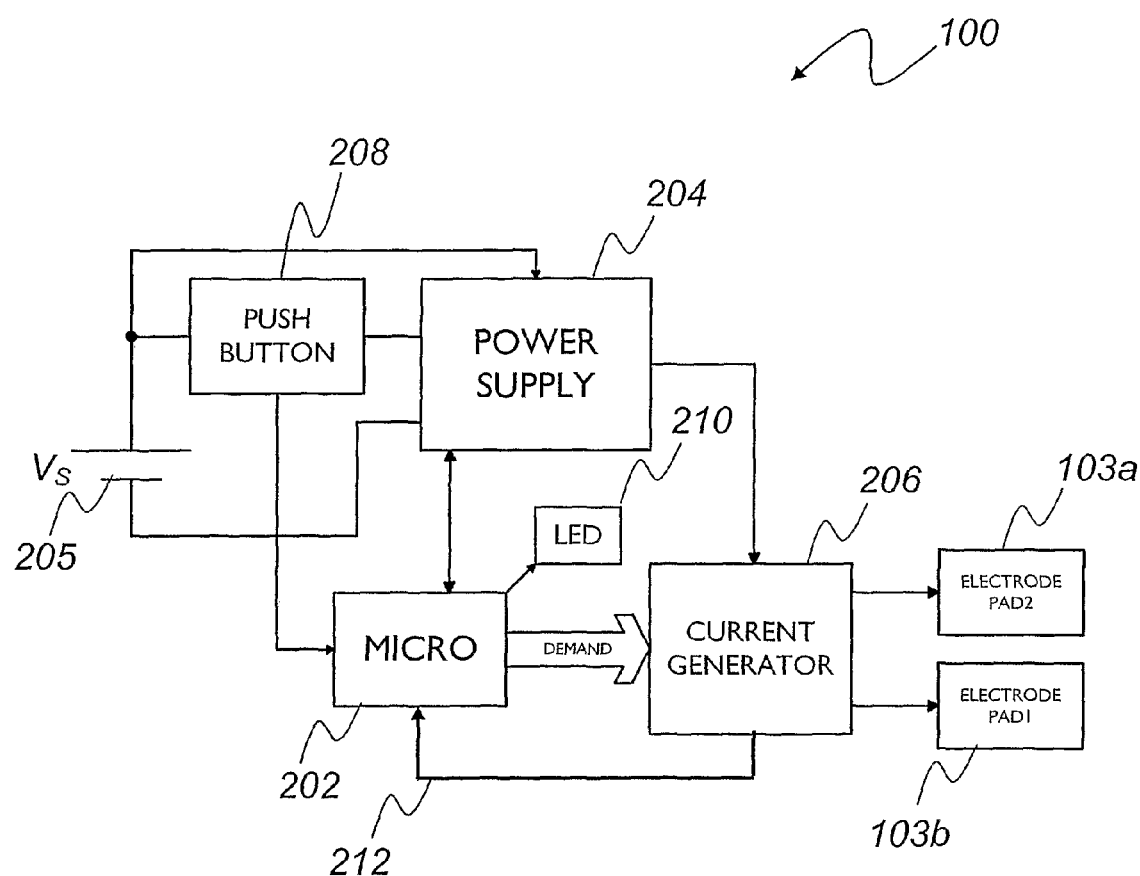
FIG. 2 is a schematic diagram of the circuitry in the control unit of the microcurrent therapy device of FIG. 1.

FIG. 1 shows a microcurrent therapy device 1 according to the present invention. A control unit 100 is connected via first and second output wires 101a, 101b to first and second input wires 102a, 102b of first and second electrodes 103a, 103b via connector 104. FIG. 2 shows a schematic representation of the internal components of the control unit 100 of FIG. 1.

Electrical current is output by the control unit 100 to pass along a first output wire 101a through a first connector 104a, along a first input wire 102a to the first electrode 103a, through tissue located against the electrodes 103a, 103b and into the second electrode 103b, along the second input wire 102b, through a second connector 104b, along the second output wire 101b and into the control unit 100. The direction of current flow can be in either direction and, depending upon the direction of current flow, one of the electrodes 103a, 103b will be a source electrode from which current is output into tissue, whilst the other electrode will be a receiving electrode into which current is received from the tissue. The control unit 100 is configured to pass the current at a predefined current level from the first electrode 103a to the second electrode 103b by controlling the voltage so that the supplied current is set at the predefined level. The predefined levels of current are set according to predefine current levels stored in treatment programs contained in memory in the control unit 100. The control unit 100 and electrodes 103a, 103b may be integrated into a single integrated unit, for example into a dressing which can be applied to tissue.

A microcontroller 202 is supplied with electrical power from a battery 205 with supply voltage Vs via a power supply 204. The microcontroller 202 is connected to a current generator 206 to control the current level that is output to the electrodes 103a, 103b. The current generator 206 is also connected directly to the power supply 204 to receive electrical current at the output voltage of the power supply 204. The current generator 206 outputs a particular level of current between the electrodes 103a, 103b to the microcontroller 202. A push button switch 208 is connected to the power supply 204 and microcontroller 202 to control the on/off status of the control unit 100. A light emitting diode (LED) 210 is also connected to and controlled by the microcontroller 202 to provide visual feedback to a user of the therapy device 1.

The current generator 206 is configured to output electrical current between the electrodes 103a, 103b at a level demanded of it by the microcontroller 202. The microcontroller 202 comprises memory stored with pre-defined programs of waveforms which have been deemed to be effective in treating damaged tissue. Thus, the microcontroller 202 demands a particular current level to be output from the current generator 206 according to the pre-defined programs which are stored within the microcontroller 202. Examples of programs which are effective in treating damaged tissue are described in the present applicant's co-pending United Kingdom patent nos. 2406519, 2432323, 2432320, 2432321 and 2432322, which are herein incorporated by reference.

Figure 3:
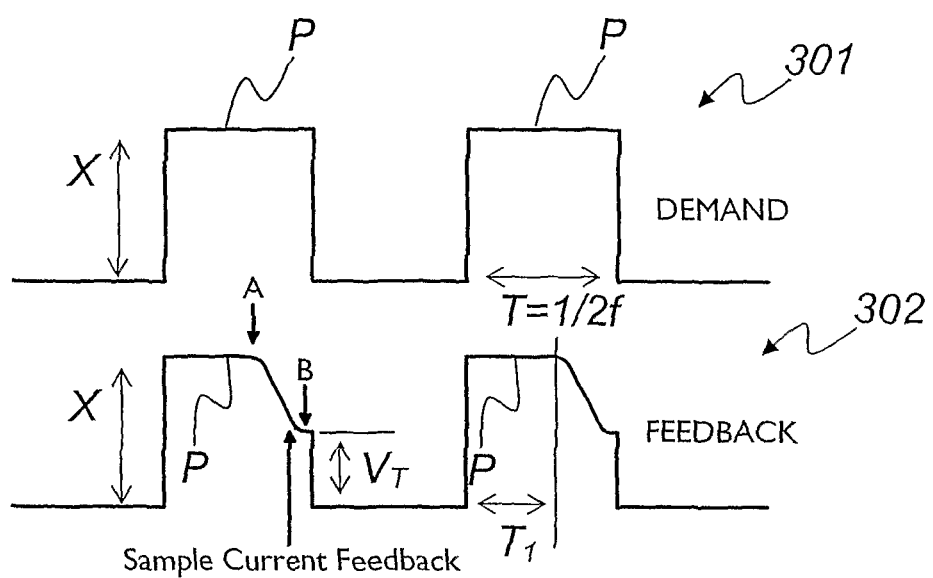
FIG. 3 is a diagram of idealised and actual waveforms of the current output by the control unit shown in FIG. 2.

FIG. 3 shows simplified waveforms of an idealised demanded current waveform 301 and an actual supplied current waveform 302 which passes between the electrodes 103a, 103b. As shown in FIG. 3, the idealised waveform 301 is a square-tooth waveform having a particular amplitude X and frequency f of pulse P. Thus, the duration of the supplied current over a particular time period is fixed for a particular level of current being supplied. As mentioned above, the actual current that passes between the electrodes is measured by the current generator 206 and this information is passed to the microcontroller 202. The current generator 206 comprises a feedback loop to vary the voltage supplied across the electrodes to keep the current at the demanded level for the particular time period.

The impedance presented by tissue and electrodes 103a, 103b is approximated to have resistive and capacitive components. Providing good electrical contact is made between the electrodes and the tissue, the electrodes 103a, 103b will be able to promote efficient ion creation in the tissue and the current generator 206 can maintain current according to the idealised waveform. However, if the electrodes 103a, 103b are not properly connected to the current generator 206 or the electrodes 103a, 103b are not in effective contact with the tissue, the impedance presented by the electrodes 103a, 103b and tissue combination will be higher than expected and the current generator 206 will attempt to increase the voltage across the electrodes 103a, 103b to keep the current at the pre-defined level.

The supply voltage $V_s$ from the battery 205 is fed to the power supply 204. The supply voltage has a maximum level $V_S$. The power supply 204 may (or may not) boost the supply voltage $V_s$ to a higher level. The power supply therefore has a maximum level of output voltage (which may be higher than the supply voltage $V_s$) to be output to the current generator 206. This maximum level of output voltage cannot be exceeded. Thus, if the resistance of the tissue and electrode combination exceeds a particular level, the current generator will no longer be able to increase the voltage across the electrodes beyond the maximum level and the current passing between the electrodes 103a, 103b will fall towards the end of a pulse. This is shown as a current drop in the current pulse P of the actual waveform 302 depicted in FIG. 3. Prior to point A, the capacitive nature of the tissue and electrodes 103a, 103b means that, despite the tissue and electrode resistance being too high, the predefined level of current can still be achieved. However, as shown by the drop in the actual waveform 302, between points A and B, the current gradually falls until it reaches a lower resistively limited value at point B. The current falls because the current generator 206 cannot increase the voltage across the electrodes 103a, 103b any higher than the maximum level after time A, so the capacitive potential presented by the charge stored in the electrodes 103a, 103b and tissue gradually drops as the charge passes our of the tissue through the electrodes 103a, 103b.

The microcontroller 202 is configured to detect any drop in the actual supplied current before the end of the current pulse via measurement of the current and voltage regulated by the current generator 206 and passed back to the microprocessor 202 via feedback line 212. The microcontroller 202 comprises an analogue to digital converter (ADC) to sample analogue current feedback and voltage feedback. When the actual current therefore falls below a threshold $V_T$ defined with respect to the demanded current beyond a particular point in time $T_1$ of the current pulse P in the actual waveform 302, a fault counter has a one value added to it. The counter is implemented as a register in the microcontroller 202. When the actual supplied current is above the threshold defined with respect to the idealised waveform for a predefined time period, then a one valve is subtracted from the fault counter (only if the fault counter is greater than zero). The microcontroller 202 is configured to check whether the fault counter exceeds a particular value (for example a value of 5). If the fault counter exceeds a fault threshold value, then the LED 210 is activated and/or its flash rate is changed by the microcontroller 202 to give a visual indication to a user of the therapy device 1 that there is a problem with passing current through the tissue. For example, this problem might be as a result of a bad connection between the control unit and the electrodes or between the electrodes and tissue. The function of the fault counter is to prevent activation of the visual indicator for a one-off fault, for example as a result of an occasional glitch in the electrode/tissue connection.

The counter provides a form of filtering on the fault indicator to ensure that faulty trips of the fault indicator do not occur. Of course, it will be appreciated that for an analogue current waveform, the current level may be negative, i.e. the current is passing in an opposite direction between the electrodes 103a, 103b. This will mean that a fault is indicated by a rise from a minimum level of the actual supplied current. The change in actual supplied current can be detected for both positive and negative parts of the current waveform at a particular point in the current pulse P, i.e. towards the end of a pulse.

Examples of detection levels used when there is a positive current pulse might be:—
- a demanded current target of 40 µA might have a threshold of 25 µA;
- a demanded current of 50 µA might have a threshold of 40 µA; and
- a demanded current of 100 µA might have a threshold of 90 µA.

The aforementioned levels would be negative if a negative current pulse was being supplied to the electrodes 103a, 103b.

In an alternative embodiment of the invention, the microprocessor 202 averages the current or voltage difference with respect to the idealised waveform over a predefined time period at the end of the pulse to give a variable value corresponding to the quality of the signal output. Thus, rather than a single bi-polar indication of the electrical signal quality, a variable value is used to give a graduated indication of the signal quality, for example via a plurality of LEDs or an LCD display (either a displayed value or level indicator).

A drop in the current with respect to the idealised waveform can be for a number of reasons, for example: battery charge becoming low, incorrect placement of electrodes (e.g. too large a separation or insufficient tissue contact) and inadequate connection between the electrodes and the control unit etc.

The microcontroller 202 is also configured to detect the voltage being supplied to the current generator 206 and provide an indication when the voltage to the current generator 206 is at its maximum towards the end of a current pulse, thereby indicating that no further current can be supplied and that there is a fault with the connection of the control unit 100 to the electrodes 103a, 103b.

A further fault is detected by the microcontroller 202 detecting a sudden drop in the voltage supplied to the current generator 206 at anytime during the current pulse. This might indicate a shorting of the electrodes. In this scenario, the demanded current would be set at a particular level, but, in an attempt to supply this current when there is a short between the electrodes, the voltage level demanded by the current generator 206 would drop to a very low level and this is detected as falling below a particular threshold voltage, thereby indicating to the microcontroller 202 that there is a short between the electrodes 103a, 103b.

It will be understood that the present invention has been described purely by way of example and modifications of detail can be made within the scope of the invention as defined by the appendent claims.

The invention claimed is:

1. A microcurrent therapy device, comprising:
   a control unit adapted to output an electrical signal to an electrode adapted to contact tissue, the current and voltage of the electrical signal being supplied according to a predefined treatment waveform selected by a user, wherein the control unit comprises a current generator, connected to the electrode,
   wherein the control unit is further adapted to:
      measure the current and voltage of the electrical signal being supplied,
      detect a lowering in the current of the electrical pulse being supplied by the current generator below a first threshold, which is defined as being a value lower than the expected current of the predefined waveform, and a lowering in the voltage of the electrical pulse being supplied below a second threshold which is defined as being a value lower than the expected voltage of the predefined waveform; and
      generate a warning when the current or voltage deviates from the current or voltage of the predefined waveform by an amount which is greater than the predefined thresholds in a predefined number of successive pulses in a predefined time period,
   wherein the current supplied by the control unit is in the range of 0 to 1000 µA.

2. The device of claim 1, wherein the warning includes activating a visual warning, such as illuminating a light emitting diode, or an audible warning, or a mechanical warning, such as a vibration.

3. The device of claim 1, wherein the control unit is adapted to detect a rise in the voltage of the electrical pulse being supplied above a threshold which is defined as being a value higher than the expected voltage of the predefined waveform.

4. The device of claim 1, wherein the control unit is adapted to detect that the voltage of the electrical pulse being supplied has reached a set maximum threshold voltage.

5. The device of claim 4, wherein the control unit is adapted to detect the voltage supplied to a current generator and comparing it to the threshold.

6. The device of claim 1, wherein the control unit is adapted to detect the difference in the current and/or voltage within a predefined time from the end of the electrical pulse.

7. The device of claim 1, wherein the control unit is a microprocessor or an ASIC.

8. A tissue dressing comprising the microcurrent therapy device of any one of the preceding claims.

9. A method for verifying the electrical output of a microcurrent therapy device, comprising:
   measuring the current and/or voltage of an electrical pulse being supplied to an electrode adapted to contact tissue, the current and/or voltage being supplied according to a predefined treatment waveform selected by a user; wherein the control unit comprises a current generator, connected to the electrode,
   detecting a lowering in the current of the electrical pulse being supplied by the current generator below a first threshold, which is defined as being a value lower than the expected current of the predefined waveform, and a lowering in the voltage of the electrical pulse being supplied below a second threshold which is defined as being a value lower than the expected voltage of the predefined waveform; and
   generating a warning when the current or voltage deviates from the current or voltage of the predefined waveform by an amount which is greater than the predefined threshold in a predefined number of successive pulses in a predefined time period
   wherein the current supplied by the control unit is in the range of 0 to 1000 µA.

10. The method of claim 9, wherein the warning includes activating a visual warning, such as illuminating a light emitting diode, or an audible warning, or a mechanical warning, such as a vibration.

11. The method of claim 9, wherein the step of detecting comprises detecting the current output by a current generator and comparing it to the threshold.

12. The method of claim 9, wherein the output of the current generator is connected to an electrode in contact with tissue.

13. The method of claim 9, wherein the step of detecting comprises detecting a rise in the voltage of the electrical pulse being supplied above a threshold which is defined as being a value higher than the expected voltage of the predefined waveform.

14. The method of claim 9, wherein the step of detecting comprises detecting that the voltage of the electrical pulse being supplied has reached a set maximum threshold voltage.

15. The method of claim 14, wherein the step of detecting comprises detecting the voltage supplied to a current generator and comparing it to the threshold.

16. The method of claim 9, wherein the step of detecting comprises detecting the difference in the current and/or voltage within a predefined time from the end of the electrical pulse.

17. The method of claim 9, wherein the step of detecting comprises digitally filtering the electrical pulse being supplied, prior to the detecting step.

18. The method of claim 9, wherein the electrical pulse of the predetermined waveform comprises a square-tooth pulse.

* * * * *